(12) United States Patent
Kent

(10) Patent No.: US 10,100,594 B2
(45) Date of Patent: Oct. 16, 2018

(54) CONTROL SYSTEM AND A METHOD FOR MONITORING A FILTER IN AN UNDERWATER HYDROCARBON WELL

(71) Applicant: GE Oil & Gas UK Limited, Nailsea, Bristol (GB)

(72) Inventor: Ian John Kent, North Somerset (GB)

(73) Assignee: GE OIL & GAS UK LIMITED, Bristol (GB)

( * ) Notice: Subject to any disclaimer, the term of this patent is extended or adjusted under 35 U.S.C. 154(b) by 0 days.

(21) Appl. No.: 15/655,149

(22) Filed: Jul. 20, 2017

(65) Prior Publication Data

US 2017/0314357 A1    Nov. 2, 2017

Related U.S. Application Data

(63) Continuation-in-part of application No. 14/316,931, filed on Jun. 27, 2014.

(30) Foreign Application Priority Data

Jun. 27, 2013  (GB) .................................. 1311407.9

(51) Int. Cl.
*G01N 15/08* (2006.01)
*E21B 33/035* (2006.01)
(Continued)

(52) U.S. Cl.
CPC .......... *E21B 33/0355* (2013.01); *B01D 65/10* (2013.01); *E21B 47/06* (2013.01); *G01N 15/0826* (2013.01); *G01N 2015/084* (2013.01)

(58) Field of Classification Search
CPC ......... G01N 15/0826; G01N 2015/084; B01D 65/10; E21B 33/0355; E21B 47/06
See application file for complete search history.

(56) References Cited

U.S. PATENT DOCUMENTS 3,282,428 A * 11/1966 Rosaen .................. B01D 29/15
                                                  210/132
3,336,793 A *  8/1967 Wainwright ........... B01D 35/00
                                                   73/38

(Continued)

FOREIGN PATENT DOCUMENTS

DE       102008027664 A1 * 12/2009 .............. E21F 17/08

OTHER PUBLICATIONS

First Office Action and search issued in connection with related CN Application No. 201410445600.9 dated Mar. 1, 2017.

*Primary Examiner* — David Bolduc
(74) *Attorney, Agent, or Firm* — GE Global Patent Operation

(57) ABSTRACT

A control system for monitoring a filter in a subsea control module (SCM) of an underwater hydrocarbon well is presented. The control system includes an upstream pressure transducer disposed upstream of a filter of the SCM and configured to sense an upstream pressure. The control system further includes a downstream pressure transducer disposed downstream of the filter and configured to sense a downstream pressure. Furthermore, the control system includes a subsea electronics module (SEM) coupled to the upstream pressure transducer and the downstream pressure transducer. The SEM is configured to determine average pressure differential values at different instances based on the upstream pressure and the downstream pressure. Moreover, the control system also includes a master control station (MCS) coupled to the SEM and configured to predict a filter maintenance generate an indication of the predicted filter maintenance due time for an operator of the underwater hydrocarbon well.

20 Claims, 5 Drawing Sheets

(51) Int. Cl.
*E21B 47/06* (2012.01)
*B01D 65/10* (2006.01)

(56) References Cited

U.S. PATENT DOCUMENTS

| | | | | |
|---|---|---|---|---|
| 3,442,384 | A * | 5/1969 | Downey | B01D 35/143 210/90 |
| 4,636,934 | A * | 1/1987 | Schwendemann | E21B 33/0355 137/624.18 |
| 4,874,002 | A * | 10/1989 | Sundholm | B08B 9/0325 134/111 |
| 5,036,698 | A * | 8/1991 | Conti | B01D 46/0086 116/DIG. 25 |
| 5,131,932 | A * | 7/1992 | Glucksman | B01D 46/46 55/471 |
| 5,236,601 | A * | 8/1993 | Snell | B01D 37/04 210/741 |
| 5,702,592 | A * | 12/1997 | Suri | B01D 35/143 116/268 |
| 5,738,172 | A * | 4/1998 | van Mook | E21B 33/0355 166/205 |
| 6,247,536 | B1 * | 6/2001 | Leismer | E21B 34/066 166/305.1 |
| 6,306,291 | B1 | 10/2001 | Lueck | |
| 7,487,837 | B2 * | 2/2009 | Bailey | E21B 33/085 166/345 |
| 8,826,988 | B2 * | 9/2014 | Gray | E21B 23/04 166/338 |
| 2002/0066309 | A1 * | 6/2002 | Tubel | E21B 23/03 73/152.54 |
| 2002/0066596 | A1 * | 6/2002 | Judge | E21B 21/001 175/5 |
| 2003/0078751 | A1 * | 4/2003 | Juhasz | B01D 46/44 702/114 |
| 2003/0094419 | A1 * | 5/2003 | Vickio, Jr. | B08B 9/0323 210/741 |
| 2004/0007392 | A1 * | 1/2004 | Judge | E21B 21/001 175/206 |
| 2004/0216884 | A1 * | 11/2004 | Bodine | E21B 33/0355 166/335 |
| 2005/0039923 | A1 * | 2/2005 | Howe | E21B 33/0355 166/368 |
| 2006/0129365 | A1 * | 6/2006 | Hammond | E21B 49/008 703/10 |
| 2008/0110674 | A1 * | 5/2008 | Jones | E21B 7/062 175/25 |
| 2008/0262736 | A1 * | 10/2008 | Thigpen | E21B 43/128 702/9 |
| 2008/0264646 | A1 * | 10/2008 | Sten-Halvorsen | E21B 33/0355 166/360 |
| 2009/0038805 | A1 * | 2/2009 | Parks | E21B 33/0355 166/341 |
| 2009/0084164 | A1 * | 4/2009 | Lowery | G01F 1/36 73/38 |
| 2009/0126798 | A1 * | 5/2009 | Mather | E21B 41/0021 137/12 |
| 2009/0151470 | A1 * | 6/2009 | Puppini | A61M 1/34 73/861 |
| 2009/0188862 | A1 * | 7/2009 | Nikolic | A61K 9/08 210/637 |
| 2009/0288836 | A1 * | 11/2009 | Goodall | F16L 1/26 166/336 |
| 2009/0294123 | A1 * | 12/2009 | Mescall | E21B 34/063 166/250.01 |
| 2010/0161250 | A1 * | 6/2010 | Tanju | F15B 19/005 702/51 |
| 2010/0252260 | A1 * | 10/2010 | Fowler | F17D 1/17 166/275 |
| 2011/0120722 | A1 * | 5/2011 | Scranton | E21B 33/0355 166/360 |
| 2011/0126912 | A1 * | 6/2011 | Grimseth | E21B 33/0355 137/1 |
| 2011/0139459 | A1 * | 6/2011 | Williams | E21B 43/0107 166/338 |
| 2011/0302911 | A1 * | 12/2011 | Coonrod | F04B 17/003 60/369 |
| 2012/0160329 | A1 * | 6/2012 | MacKenzie | E21B 43/01 137/1 |
| 2012/0279720 | A1 * | 11/2012 | Whitby | E21B 33/0355 166/363 |
| 2013/0092389 | A1 * | 4/2013 | Du | E21B 17/01 166/367 |
| 2014/0379626 | A1 * | 12/2014 | Hessmer | G06N 5/04 706/46 |

* cited by examiner

CONTROL SYSTEM AND A METHOD FOR MONITORING A FILTER IN AN UNDERWATER HYDROCARBON WELL

CROSS-REFERENCE TO RELATED APPLICATIONS

This application is a continuation-in-part of U.S. application Ser. No. 14/316,931 filed on Jun. 27, 2014, the entire contents of which are hereby incorporated by reference.

BACKGROUND

Embodiments of the present specification relate to monitoring a hydraulic fluid filter and, more particularly, to a control system and a method for monitoring a filter in an underwater (for example subsea) hydrocarbon well facility.

In offshore hydrocarbon well control systems, the main equipment of a typical system configuration includes: a master control station, which provides the operator interface with subsea equipment and displays the current state of various subsurface equipment, subsea valves and sensor information enabling the operator to control the system; an umbilical cable, which connects the master control station to the equipment installed on the seabed and incorporates a communication link which carries control signals to the subsurface equipment and transfers information on the status of the subsurface equipment to the master control station; a subsea control module, which receives commands from the master control station and controls subsea processes, provides the hydraulic power to actuate valves and transmits status data on subsea equipment and sensor data to the master control station; a subsea electronics module, housed within the subsea control module and which typically is a microprocessor based electronics unit that houses a set of printed circuit boards, the functions of which include communication with the master control station (receiving control information from, and transmitting sensor data to, the master control station), interfacing with subsurface sensors and controlling valves and hydraulics; and a tree installed on the seabed, to which is fitted the subsurface electric and hydraulic equipment needed to control the flow of fluids from or to the well together with a sensor pack, to determine the state of the tree equipment, well head components and fluid flowing from or to the well.

Hydraulic fluid is supplied to a subsea control module in a redundant manner in order to provide power for operating the hydraulic valves located on subsea trees and manifolds. In order to remove particulate matter from the fluid, the fluid is passed through filters. Pressure transducers are normally located downstream of the filters for monitoring the incoming pressure of the fluid, and then selector valves allow the operator to select which of the redundant supplies is used for valve operation. The selected fluid is then used as a common supply for operations within the subsea control module, and a pressure transducer is used to monitor this supply pressure.

With this configuration of transducers and filters, there is no method to monitor the health (contamination levels) and hence life of the filters. If there is no method for assessing the contamination of such filters when a subsea control module is deployed and the subsea control module is operated until problems are experienced, if the filters become blocked, this could result in discontinuity in operations of the hydrocarbon well, and cause lack of hydrocarbon production for a period of time until the module can be recovered and a replacement installed.

BRIEF DESCRIPTION

In accordance with one embodiment of the present specification, a control system for monitoring a filter in a subsea control module of an underwater hydrocarbon well is presented. In the subsea control module, an input of the filter is connected to a hydraulic fluid source to receive a hydraulic fluid and where the filter is configured to filter the hydraulic fluid. The control system includes an upstream pressure transducer disposed upstream of the filter and configured to sense an upstream pressure of the hydraulic fluid. The control system further includes a downstream pressure transducer disposed downstream of the filter and configured to sense a downstream pressure of the hydraulic fluid. Furthermore, the control system includes a subsea electronics module (SEM) coupled to the upstream pressure transducer and the downstream pressure transducer. The SEM is configured to determine average pressure differential values at different instances based on the upstream pressure and the downstream pressure. Moreover, the control system also includes a master control station (MCS) coupled to the SEM and configured to: receive the average pressure differential values from the SEM, determine a rate of change of the average pressure differential based on the average pressure differential values, extrapolate the rate of change of the average pressure differential to obtain an extrapolated average pressure differential, predict a filter maintenance due time based on the extrapolated average pressure differential, the rate of change of the average pressure differential, and a target maintenance pressure differential, and generate an indication of the predicted filter maintenance due time for an operator of the underwater hydrocarbon well.

In accordance with another embodiment of the present specification, a control system for monitoring a filter in a subsea control module of an underwater hydrocarbon well is presented. In the subsea control module, an input of the first filter is connected to a first hydraulic fluid source to receive a first hydraulic fluid and an input of the second filter is connected to a second hydraulic fluid source to receive a second hydraulic fluid. The control system includes a first upstream pressure transducer disposed upstream of the first filter and configured to sense a first upstream pressure of the first hydraulic fluid, where the first filter is disposed in a first hydraulic flow path of the subsea control module, The control system further includes a second upstream pressure transducer disposed upstream of the second filter and configured to sense a second upstream pressure of the second hydraulic fluid, where the second filter is disposed in a second hydraulic flow path of the subsea control module. The control system further includes a first downstream pressure transducer coupled directly to an output of the first filter and configured to sense a first downstream pressure of the first hydraulic fluid. The control system further includes a second downstream pressure transducer coupled directly to an output of the second filter and configured to sense a second downstream pressure of the second hydraulic fluid. The control system further includes an SEM coupled to the first upstream pressure transducer, the first downstream pressure transducer, the second upstream pressure transducer, and the second downstream pressure transducer. The SEM is configured to determine average pressure differential values at different instances based the first upstream pressure and the first downstream pressure or the second upstream pressure and the second downstream pressure. Moreover, the control system also includes an MCS coupled to the SEM. The MCS is configured to receive the average pressure differential values from the SEM, determine a rate of change of the average pressure differential based on the average pressure differential values, extrapolate the rate of change of the average pressure differential to obtain an extrapolated average pressure differential; predict a filter maintenance due time based on the extrapolated average pressure differential, the rate of change of the average pressure differential, and a target maintenance pressure differential, generate an indication of the predicted filter maintenance due time for an operator of the underwater hydrocarbon well.

In accordance with yet another embodiment of the present specification, a method for monitoring a filter in a subsea control module of an underwater hydrocarbon well is presented. In the subsea control module, an input of the filter is connected to a hydraulic fluid source to receive a hydraulic fluid. The method includes receiving average pressure differential values from an SEM, where the SEM is coupled to an upstream pressure transducer disposed upstream of the filter and a downstream pressure transducer disposed downstream of the filter. The method further includes determining a rate of change of the average pressure differential based on the average pressure differential values. The method also includes extrapolating the rate of change of the average pressure differential to obtain an extrapolated average pressure differential. Furthermore, the method includes predicting a filter maintenance due time based on the extrapolated average pressure differential, the rate of change of the average pressure differential, and a target maintenance pressure differential. Moreover, the method includes generating an indication of the predicted filter maintenance due time for an operator of the underwater hydrocarbon well.

DRAWINGS

These and other features, aspects, and advantages of the present specification will become better understood when the following detailed description is read with reference to the accompanying drawings in which like characters represent like parts throughout the drawings, wherein.

DETAILED DESCRIPTION

Unless defined otherwise, technical and scientific terms used herein have the same meaning as is commonly understood by one of ordinary skill in the art to which this disclosure belongs. In the following specification and the claims, the singular forms "a", "an" and "the" include plural referents unless the context clearly dictates otherwise. As used herein, the term "or" is not meant to be exclusive and refers to at least one of the referenced components being present and includes instances in which a combination of the referenced components may be present, unless the context clearly dictates otherwise.

As used herein, the terms "may" and "may be" indicate a possibility of an occurrence within a set of circumstances; a possession of a specified property, characteristic or function; and/or qualify another verb by expressing one or more of an ability, capability, or possibility associated with the qualified verb. Accordingly, usage of "may" and "may be" indicates that a modified term is apparently appropriate, capable, or suitable for an indicated capacity, function, or usage, while taking into account that in some circumstances, the modified term may sometimes not be appropriate, capable, or suitable.

Approximating language, as used herein throughout the specification and claims, may be applied to modify any quantitative representation that could permissibly vary without resulting in a change in the basic function to which it is related. Accordingly, a value modified by a term or terms, such as "about", and "substantially" is not to be limited to the precise value specified. Here and throughout the specification and claims, range limitations may be combined and/or interchanged; such ranges are identified and include all the sub-ranges contained therein unless context or language indicates otherwise.

Figure 1:
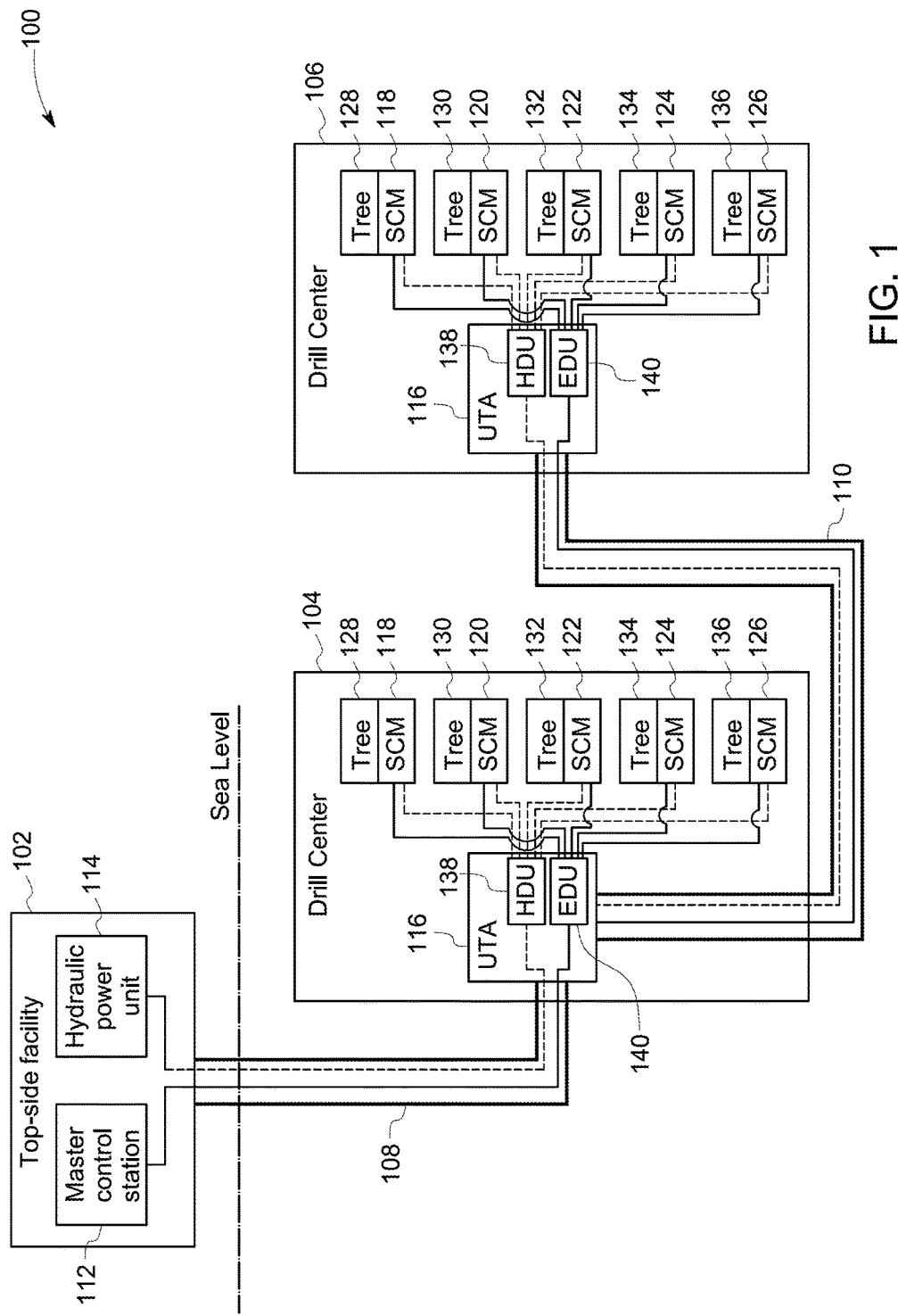
FIG. 1 is a block diagram of an underwater hydrocarbon well facility, in accordance with one embodiment of the present specification.

FIG. 1 is a block diagram of an underwater hydrocarbon well facility 100, in accordance with one embodiment of the present specification. In some embodiments, the underwater hydrocarbon well facility 100 includes a top-side facility 102 and drill centers 104 and 106. The top-side facility 102 is disposed on a surface above a sea level. Each of the drill center 104, 106 represents an underwater hydrocarbon well. Although, two drill centers 104, 106 are shown in the underwater hydrocarbon well facility 100, the underwater hydrocarbon well facility 100 with any number of drill centers is also envisioned. The top-side facility 102 is coupled to the drill center 104 via a main umbilical 108. The main umbilical 108 terminates at the drill center 104. The drill center 104 is coupled to the drill center 106 via an infield composite umbilical 110. The umbilicals 108 and 110 facilitate electrical and hydraulic power to the drill centers 104, 106. Moreover, in some embodiments, the umbilicals 108 and 110 also include cables for data communication between the top-side facility 102 and the drill centers 104, 106.

In some embodiments, the top-side facility 102 includes a master control station (MCS) 112 and a hydraulic power unit (HPU) 114 that are disposed is disposed outside the underwater hydrocarbon well. By way of example the MCS 112 and the HPU 114 are disposed on the surface above the sea level. The MCS 112 facilitates control of the underwater hydrocarbon well facility 100 and provides a user interface for an operator of the underwater hydrocarbon well facility 100. The MCS 112 includes microcontrollers, computers, programmable logic controllers (PLCs), subsea electrical power units, modems, communication equipment, or combinations thereof. In some embodiments, the computers and/or microcontrollers used in the MCS 112 may include specially programmed general purpose computer, an electronic processor such as a microprocessor, a digital signal processor, and/or a microcontroller. Various examples of the microprocessor include, but are not limited to, a reduced instruction set computing (RISC) architecture type microprocessor or a complex instruction set computing (CISC)

architecture type microprocessor. Further, the microprocessor may be a single-core type or multi-core type. Further, the computers and/or microcontrollers may include input/output ports, and a storage medium, such as an electronic memory. The HPU 114 includes pumps and PLCs for controlling flow of hydraulic fluids to the drill centers 104 and 106. In a non-limiting example, the HPU 114 may provide two levels of hydraulic pressures—low pressure at about 345 bar and high pressure at about 690 bar, to each of the drill centers 104 and 106, for example.

The drill centers 104 and 106 typically include an umbilical termination assembly (UTA) 116 and one or more subsea control modules (SCMs) such as the SCMs 118, 120, 122, 124, and 126. Reference numerals 128, 130, 132, 134, and 136 represent trees (i.e., branches of well) of drill facilities 104, 106. As depicted in FIG. 1, at least one SCM is disposed in each of the trees 128-136. Although, five trees are shown in the drill centers 104, 106, drill centers with greater or fewer than five trees are also envisioned. In some embodiments, the UTA 116 includes a hydraulic distribution unit (HDU) 138 and an electrical distribution unit (EDU) 140. The HDU 138 distributes hydraulic fluid to the SCMs 118-126 in the respective drill centers 104, 106. The EDU 140 distributes electrical power to the SCMs 118-126 in the respective drill centers 104, 106.

The SCMs 118-126 typically includes valves such as a directional control valve (DCV), filters, and actuators to control subsea processes to facilitate extraction of hydrocarbon fluids from the respective drill centers 104, 106. The SCMs 118-126 receive commands from the MCS 112, control subsea processes, provide the hydraulic power to actuate the valves, and/or transmit status data to the MCS 112. The DCVs typically require clean hydraulic fluid to facilitate control of the actuators. The filters in the SCMs 118-126 provide clean hydraulic fluid to the DCVs. During operation, the filters may block contaminants from the respective hydraulic fluids and are prone to clogging due to accumulation of the contaminants. To avoid any discontinuity in the subsea processes, it may be desirable to monitor the filters and maintain and/or replace the filters in a timely manner. Therefore, in accordance with some embodiments, the underwater hydrocarbon well facility 100 includes a control system (shown in FIGURES (FIGS. 2 and 3) for monitoring of the filters within the SCMs 118-126. Further details of the SCMs 118-126 and the control system are described in conjunction with FIGS. 2 and 3.

Figure 2:
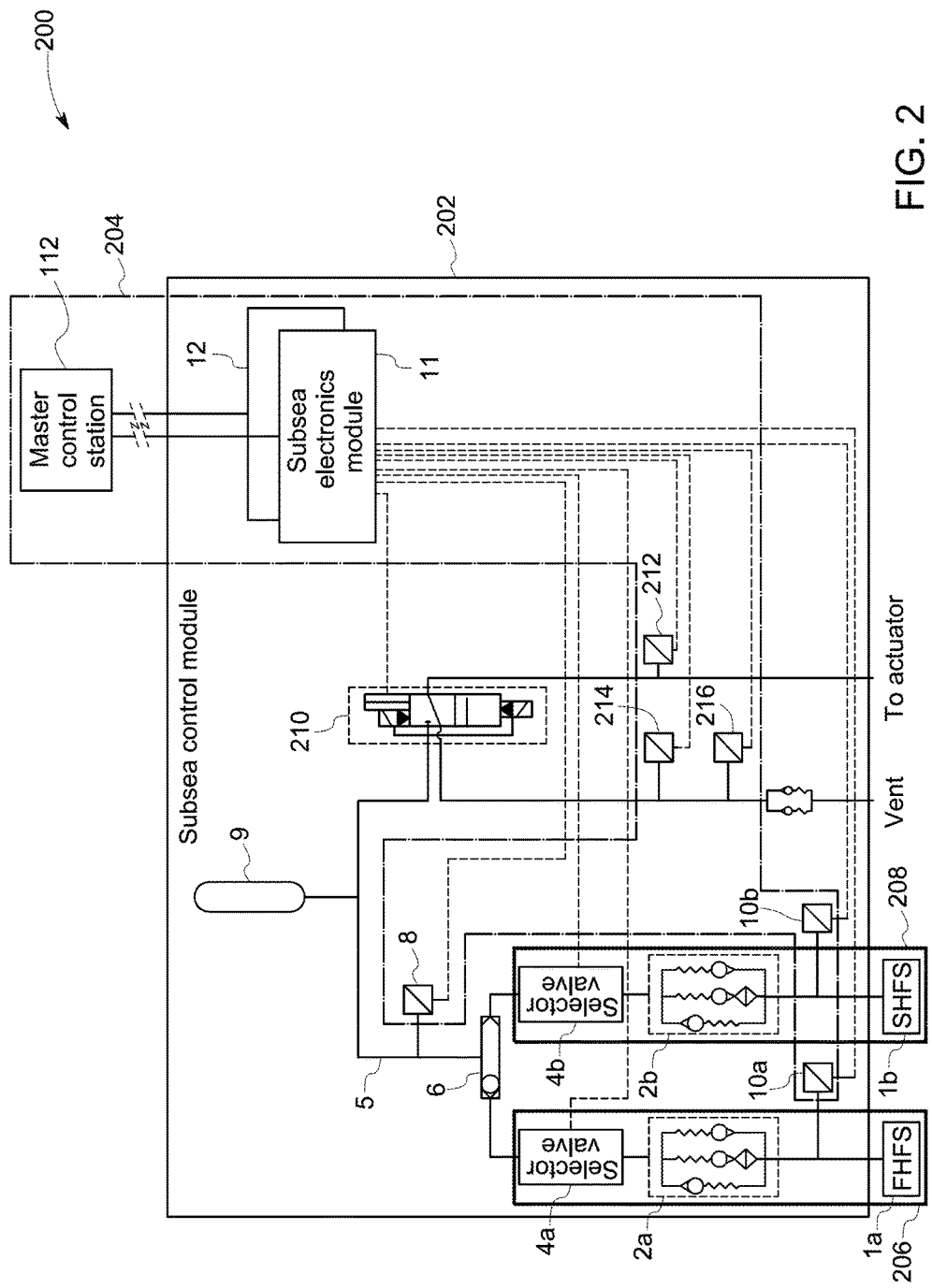
FIG. 2 is a schematic diagram of a portion of the underwater hydrocarbon well facility of FIG. 1 showing a subsea control module and a control system, in accordance with one embodiment of the present specification.

FIG. 2 is a schematic diagram of a portion 200 of the underwater hydrocarbon well facility 100 of FIG. 1, showing an SCM 202 and a control system 204, in accordance with one embodiment of the present specification. By way of example, the SCM 202 may represent one of the SCMs 118-126. The SCM 202 may include a first hydraulic fluid flow path 206 including a first hydraulic fluid source 1a, a first filter 2a, and a first selector valve 4a. The SCM 202 may also include a redundant hydraulic fluid flow path, hereinafter also referred to as, a second hydraulic fluid flow path 208 including a second hydraulic fluid source 1b, a second filter 2b, and a second selector valve 4b.

The hydraulic fluid sources 1a and 1b may be representative of hydraulic fluid conduits/pipes that carry hydraulic fluid from the HDU 138 of the respective UTA 116 (see FIG. 1) to the SCM 202. The first hydraulic fluid source 1a and the second hydraulic fluid source 1b respectively supply a first hydraulic fluid and a second hydraulic fluid to corresponding filter of the filters 2a and 2b. In some embodiments, the first hydraulic fluid is same as the second hydraulic fluid. In some embodiment, the first hydraulic fluid is different from the second hydraulic fluid. The first filter 2a and second filter 2b are operated to filter the first hydraulic fluid and the second hydraulic fluid, respectively. The selector valve 4a is coupled to an output of the first filter 2a and is configured to selectively enable or disable a flow of the first hydraulic fluid via the first filter 2a. The selector valve 4b is coupled to an output of the second filter 2b and configured to selectively enable or disable a flow of the second hydraulic fluid via the second filter 2b. The first and second hydraulic fluid flow paths 206, 208 are connected to a shuttle valve 6 to provide a common supply to an output 5. It is to be noted that at a given point of time, one of the two selector valve 4a, 4b is ON and facilitates a flow of the hydraulic fluid therethrough. Therefore, the output 5 carries the first hydraulic fluid if the selector valve 4a is ON or the second hydraulic fluid if the selector valve 4b is ON.

The first and second hydraulic fluids are supplied in a redundant manner from hydraulic fluid sources 1a and 1b. The incoming first and second hydraulic fluids are filtered by a respective one of filters 2a and 2b to remove contaminants such as particulate matter, for example. Then the hydraulic fluids may reach to respective ones of selector valves 4a and 4b, enabling supply selection to be performed, and the common supply to an output 5 is provided via the shuttle valve 6. The common supply from output 5 is fed to a manifold 9 within the SCM 202. In the SCM 202, the manifold 9 may further be coupled to a valve such as a directional control valve (DCV) 210 that controls one or more actuators (not shown). The DCV 210 typically requires clean hydraulic fluid to facilitate control of the actuators. The filters 2a, 2b provide clean hydraulic fluid to the DCV 210.

During operation, the filters 2a, 2b may block contaminants from the respective hydraulic fluids and may therefore be prone to clogging due to accumulation of the contaminants. To avoid any discontinuity in the subsea processes, it may be desirable to monitor the filters 2a, 2b and maintain and/or replace the filters in a timely manner.

To facilitate such monitoring of the filters 2a, 2b the underwater hydrocarbon well facility 100 includes the control system 204. The control system 204 includes an upstream pressure transducer, such as, a first upstream pressure transducer 10a and a second upstream pressure transducer 10b, a downstream pressure transducer 8, and one or more subsea electronics modules (SEMs) such as an SEM 11 and an SEM 12. Additionally, the MCS 112 also forms a part of the control system 204.

The upstream pressure transducer 10a, 10b is disposed upstream of the filter 2a, 2b and configured to sense an upstream pressure of the hydraulic fluid. For example, as depicted in FIG. 2, the first upstream pressure transducer 10a is disposed upstream of the first filter 2a and the second upstream pressure transducer 10b is disposed upstream of the second filter 2b. In certain embodiments, the upstream pressure transducers 10a and 10b are disposed between the respective hydraulic fluid source 1a, 1b and filters 2a, 2b, as shown in FIG. 2. The first upstream pressure transducer 10a may sense an upstream pressure of the first hydraulic fluid upstream of the filter 2a and generate an electrical signal indicative of the sensed upstream pressure of the filter 2a. The second upstream pressure transducer 10b may sense an upstream pressure of the second hydraulic fluid upstream of the filter 2b and generate another electrical signal indicative of the sensed upstream pressure of the filter 2b.

The downstream pressure transducer 8 is disposed downstream of the filters 2a, 2b and configured to sense a downstream pressure of the hydraulic fluid at the downstream of the filters 2a, 2b. In one embodiment, the downstream pressure transducer 8 is disposed downstream of the selector valves 4a, 4b. In the embodiment of FIG. 2, the downstream pressure transducer 8 is coupled to the output 5 downstream of the shuttle valve 6. In certain embodiments, the downstream pressure transducer may be disposed between the filter 2a, 2b and the selector valves 4a, 4b (see FIG. 3). The downstream pressure transducer 8 may sense a downstream pressure of the hydraulic fluid in the output 5 downstream of the filters 2a, 2b and generate another electrical signal indicative of the sensed downstream pressure.

In some embodiments, the control system 204 may also optionally include pressure transducers 212, 214, and/or 216. The pressure transducer 212 is coupled to downstream of the DCV 210 and configured to sense a pressure of the hydraulic fluid downstream of the DCV 210. As depicted in FIG. 2, the pressure transducer 212 is coupled between the DCV 210 and an actuator (not shown). The pressure transducer 212 generates an electrical signal indicative of the pressure of the hydraulic fluid downstream of the DCV 210. The pressure transducers 214, 216 are also coupled to the DCV 210. As depicted in FIG. 2, the pressure transducers 214, 216 are disposed in a flow path between the DCV 210 and a vent (not shown). The pressure transducer 212 generates an electrical signal indicative of the pressure of the hydraulic fluid in the flow path between the DCV 210 and the vent.

The subsea electronics module (SEM) 11 may be electrically coupled to the upstream pressure transducer, such as, the first and second upstream pressure transducers 10a, 10b and the downstream pressure transducer 8. In some embodiments, the SEM 11 may be coupled to the pressure transducers 212, 214, and/or 216. In certain embodiments, the control system 204 may also include a redundant SEM such as the SEM 12, which may also be coupled to the upstream pressure transducers 10a, 10b, the downstream pressure transducer 8, and/or the pressure transducers 212, 214, 216. At any given point of time, one of the SEMs 11, 12 may be active. Hereinafter, the SEM 11 is considered as active and various operations are described with respect to the SEM 11. The SEM 11 may be configured to monitor the electric signals generated by the first and second upstream pressure transducers 10a, 10b and the downstream pressure transducer 8 thereby monitoring the health of the filters 2a, 2b.

The SEM 11 receives the electric signals from the upstream pressure transducers 10a, 10b and the downstream pressure transducer 8 at different instances. By way of example, the SEM 11 may periodically or randomly receive the electric signals from the upstream pressure transducers 10a, 10b and the downstream pressure transducer 8. The SEM 11 determines instantaneous upstream and downstream pressures based on one or more parameters, for example, amplitude, frequency, and/or phase, of the receive electric signals. Based on the determined instantaneous upstream and downstream pressures, the SEM 11 may determine a minimum pressure differential, a maximum pressure differential, and an average pressure differential between the determined upstream and downstream pressures. By way of example, if the selector valve 4a is ON, the SEM 11 may determine a pressure differential ($PD_{10a/8}$) between the upstream pressure ($P_{10a}$) sensed using the upstream pressure transducer 10a and the downstream pressure sensed using the downstream pressure ($P_8$) transducer 8, by using equation (1):

$$PD_{10a/8} = P_{10a} - P_8 \qquad \text{Equation (1)}$$

Alternatively, if the selector valve 4b is ON, the SEM 11 may determine a pressure differential ($PD_{10b/8}$) between the upstream pressure ($P_{10b}$) sensed using the upstream pressure transducer 10b and the downstream pressure sensed using the downstream pressure ($P_8$) transducer 8, by using equation (2):

$$PD_{10b/8} = P_{10b} - P_8 \qquad \text{Equation (2)}$$

The SEM 11 may further determine average pressure differential values based on the pressure differential $PD_{10a/8}$ or $PD_{10b/8}$ (depending on which selector valve is ON) at different instances. By way of example, if the selector valve 4a is ON, the SEM 11 may determine the average pressure differential values of the pressure differential $PD_{10a/8}$, by using equation (3):

$$PDAVG_{10a/8} = \frac{\sum_{i=0}^{N} PD_{10a/8}}{N} \qquad \text{Equation (3)}$$

where, i indicates an instance and N indicates number of instances.

The SEM 11 may communicate the determined average pressure differential values to the MCS 112. The MCS 112 may determine a rate of change of the average pressure differential based on the average pressure differential values received from the SEM 11. The MCS 112 may further extrapolate the rate of change of the average pressure differential to obtain an extrapolated average pressure differential and predict a filter maintenance due time based on the extrapolated average pressure differential, the rate of change of the average pressure differential, and a target maintenance pressure differential. Additionally, the MCS 112 may also generate an indication of the predicted filter maintenance due time for an operator of the underwater hydrocarbon well facility 100. In some embodiments, the MCS 112 also generates an alarm indicative of an increased level of clog in the filter 2a or 2b if the rate of change of the average pressure differential exceeds a predefined threshold value. Further details of the operations performed by the MCS 112 is described in conjunction with FIGS. 4 and 5.

As the filters 2a, 2b become blocked, the differential pressure across it becomes higher. Since in use of the hydraulic circuit, flow is only sporadic (during and after valve operations), when the system is in steady state, no differential would exist, so the software within the SEM 11 is configured to monitor the peak differential pressure during each active period. When the differential pressure exceeds a threshold during a period of fluid flow, an alarm can be raised, thus alerting the operator of a potential blockage within the filter.

It should be noted from FIG. 2 that there are other components than filters 2a, 2b in the hydraulic fluid flow paths 206, 208 between each hydraulic fluid source 1a, 1b and the shuttle valve 6. These components may affect flow, and as such affect the differential pressure measured. However, these devices can be considered constants, and their effect zeroed out of the calculated differential pressure through taking baseline readings when the filter is known to be clean.

Figure 3:
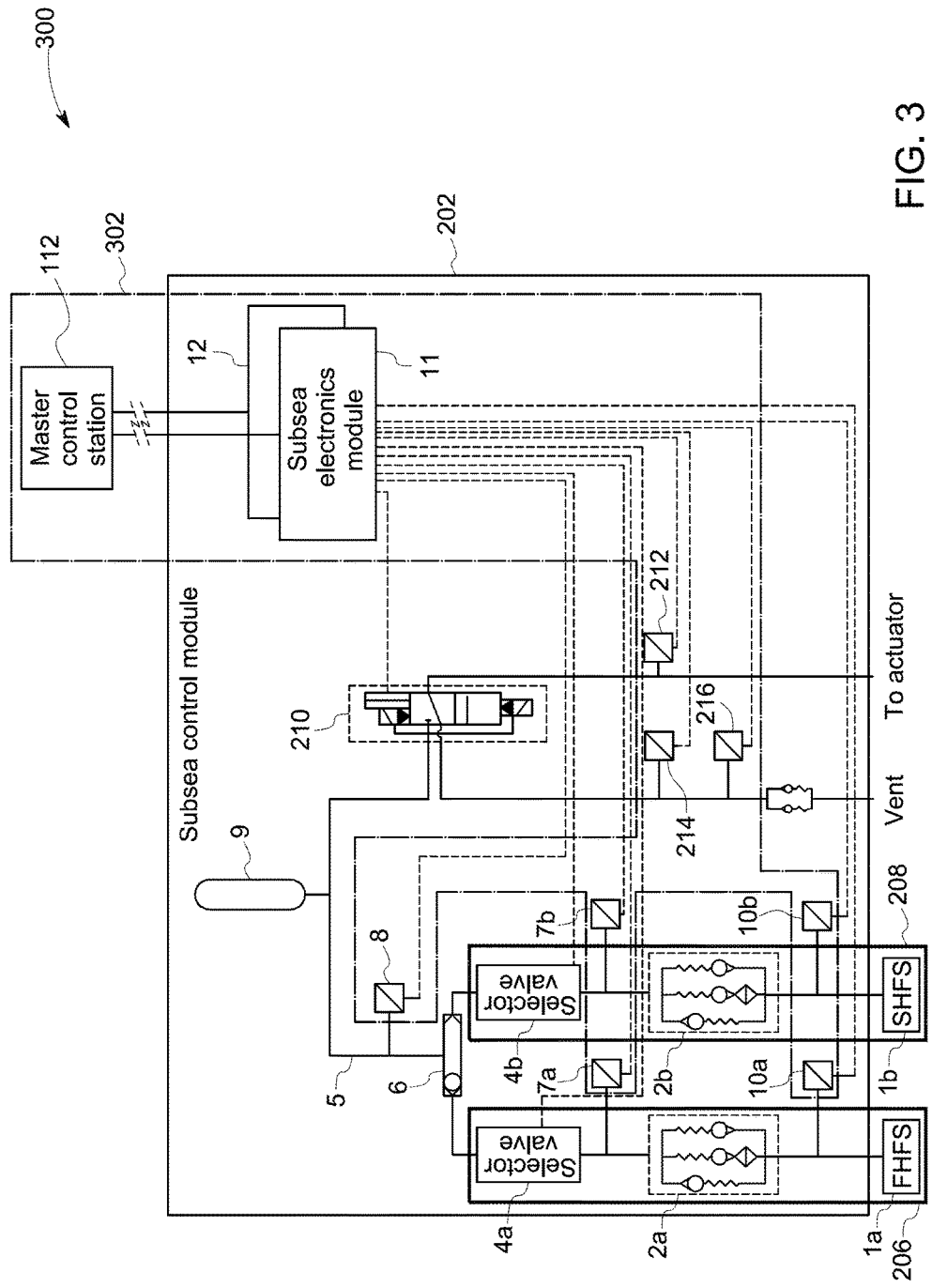
FIG. 3 is a schematic diagram of a portion of the underwater hydrocarbon well facility of FIG. 1 showing a subsea control module and a control system, in accordance with one embodiment of the present specification.

A further improvement of a control system used in the underwater hydrocarbon well facility 100 may be realised as shown in FIG. 3. FIG. 3 is a schematic diagram of a portion 300 of the underwater hydrocarbon well facility 100 of FIG. 1 showing the SCM 202 and a control system 302, in accordance with one embodiment of the present specification. The control system 302 includes certain components that are similar to the corresponding components used in the control system 204 of FIG. 2, the description of which is not repeated herein.

Additionally, the control system 302 includes one or more downstream pressure transducers such as a first downstream pressure transducer 7a disposed in the first hydraulic fluid flow path 206 and a second downstream pressure transducer 7a disposed in the second hydraulic fluid flow path 208. In certain embodiments, the first downstream pressure transducer 7a is coupled directly to an output of the first filter 2a and configured to sense a first downstream pressure of the first hydraulic fluid. In some embodiments, the term "coupled directly" as used herein refers to a connection between two components (e.g., the first downstream pressure transducer 7a and the output of the first filter 2a) without any intermediate element in a fluid flow path between the two components. Similarly, the second downstream pressure transducer 7a is coupled directly to an output of the second filter 2b and configured to sense a second downstream pressure of the second hydraulic fluid. The downstream pressure transducers 7a, 7b generate electric signals indicative of the first downstream pressure and the second downstream pressure, respectively. As previously noted, the upstream pressure transducers 10a, 10b generate electric signals indicative of the first upstream pressure and the second upstream pressure, respectively.

In the embodiment of FIG. 3, the SEM 11 is coupled to the first upstream pressure transducer 10a, the first downstream pressure transducer 7a, the second upstream pressure transducer 10b, and the second downstream pressure transducer 7b. Further, the SEM 11 is configured to determine average pressure differential values at different instances based the first upstream pressure and the first downstream pressure or the second upstream pressure and the second downstream pressure. By way of example, if the selector valve 4a is ON, the SEM 11 may determine the average pressure differential values between the first upstream pressure and the first downstream pressure, by using equation (4):

$$PDAVG_{10b/7a} = \frac{\sum_{i=0}^{N} PD_{10a/7a}}{N} \qquad \text{Equation (4)}$$

Where $PDAVG_{10b/7a}$ indicates a pressure differential between the first upstream pressure and the first downstream pressure, i indicates an instance and N indicates number of instances.

As the differential pressure that will be monitored is an analogue reading, over time a rate of change can therefore be determined. This rate of change can then be used to predict when maintenance and intervention may be required.

Embodiments of the present specification enable the contamination levels of the filters 2a, 2b within a subsea control module to be assessed whilst the module is in operation. Embodiments of the present specification further, enables the operator to be alerted of contamination and/or enables maintenance of the module to be scheduled.

The SEM 11 may communicate the determined average pressure differential values to the MCS 112. The MCS 112 predicts a filter maintenance due time based the received average pressure differential values. Additionally, the MCS 112 also generates an indication of the predicted filter maintenance due time for an operator of the underwater hydrocarbon well facility 100. Such a configuration of the control system 302 may allow monitoring of the filters 2a, 2b, and minimize or remove the potential for differential pressure inaccuracy, due to the presence of other components in the respective hydraulic fluid flow paths 206, 208. Further details of the operations performed by the MCS 112, is described in conjunction with FIGS. 4 and 5.

If a method of assessing the contamination level within the filters 2a, 2b during operation can be implemented, then subsea control module operation may be optimised, or preventative maintenance planned thus alleviating unscheduled shutdowns and loss of production. The control systems 204 and 302, in accordance with some embodiments, facilitate prediction and identification of progressive contamination of hydraulic filters 2a, 2b (see FIG. 4). This will allow enhanced subsea control module prognostics, and planning predictive replacement of such a module in the event of filter contamination.

Figure 4:
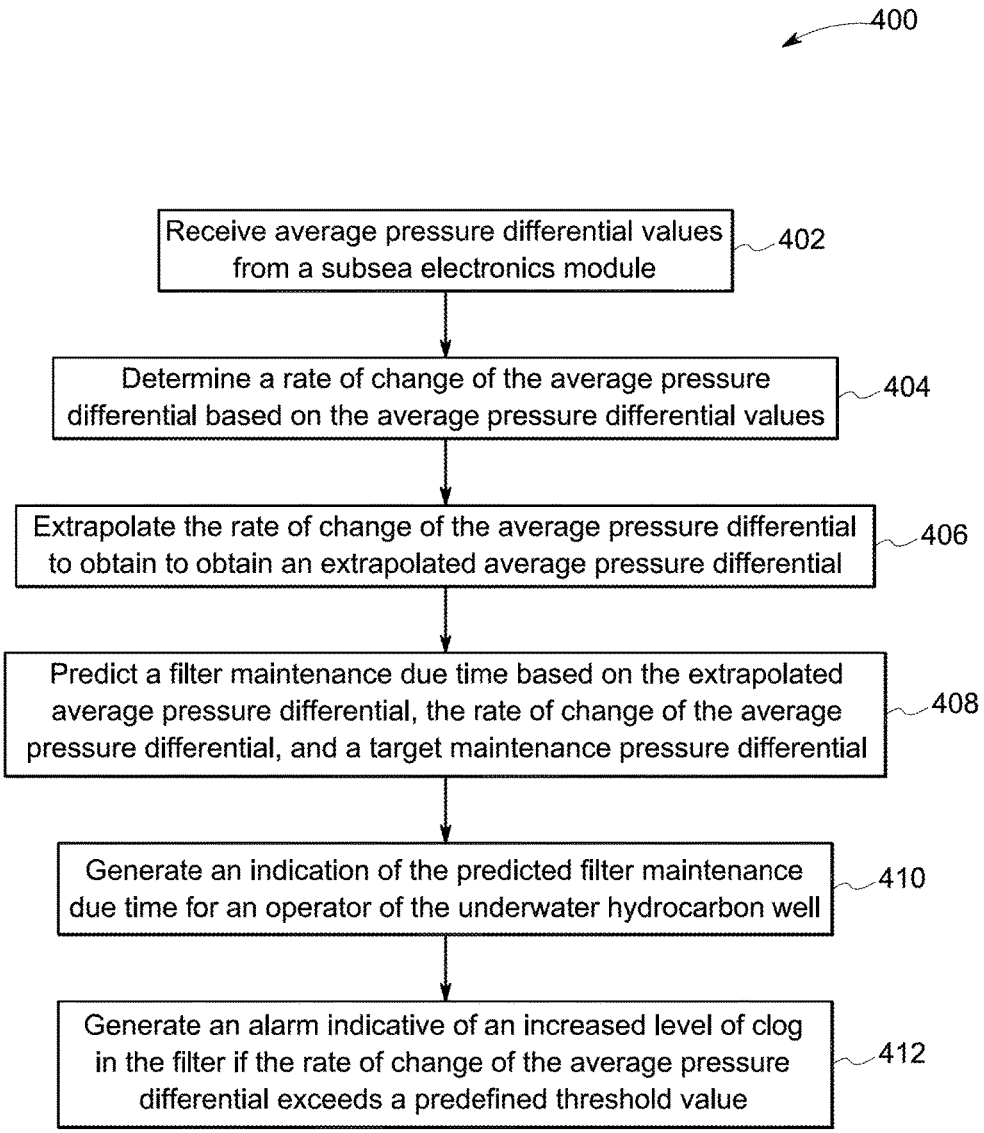
FIG. 4 is a flow diagram of a method for monitoring a filter in the subsea control module of FIG. 2 or FIG. 3, in accordance with one embodiment of the present specification.

FIG. 4 is a flow diagram of a method 400 for monitoring a filter such as one or more of the filters 2a, 2b in the SCM 202 of FIG. 2 or FIG. 3, in accordance with one embodiment. Hereinafter, the method 400 is described with reference to FIG. 2. It is to be noted that one or more embodiments of the method 400 described herein are also applicable to monitoring the filters 2a, 2b of FIG. 3 as well, without limiting the scope of the present specification. The method 400 includes steps 402-412.

At step 402, the method 400 includes receiving average pressure differential values from the SEM 11. The average pressure differential values are received by the MCS 112 from the SEM 11. As previously noted, the SEM 11 is coupled to the upstream pressure transducer 10a, 10b disposed upstream of the filters 2a, 2b and the downstream pressure transducer disposed downstream of the filters 2a, 2b. The SEM 11 determines the average pressure differential values for the filter enabled by the respective selector valves 4a, 4b. At a given point in time, one of the filters 2a, 2b is enabled. Accordingly, at step 402, the average pressure differential values corresponding to the active/enabled filter is received by the MCS 112 from the SEM 11. In some embodiments, the MCS 112 may receive the average pressure differential values periodically or randomly. In the embodiment of FIG. 2, the SEM 11 determines the average pressure differential values based on the downstream pressure sensed by the downstream pressure transducer 8 and one of the upstream pressure sensed by the upstream pressure transducers 10a or 10b. In the embodiment of FIG. 3, the SEM 11 determines the average pressure differential values based on the first upstream pressure and the first downstream pressure, or the second upstream pressure and the second downstream pressure.

Figure 5:
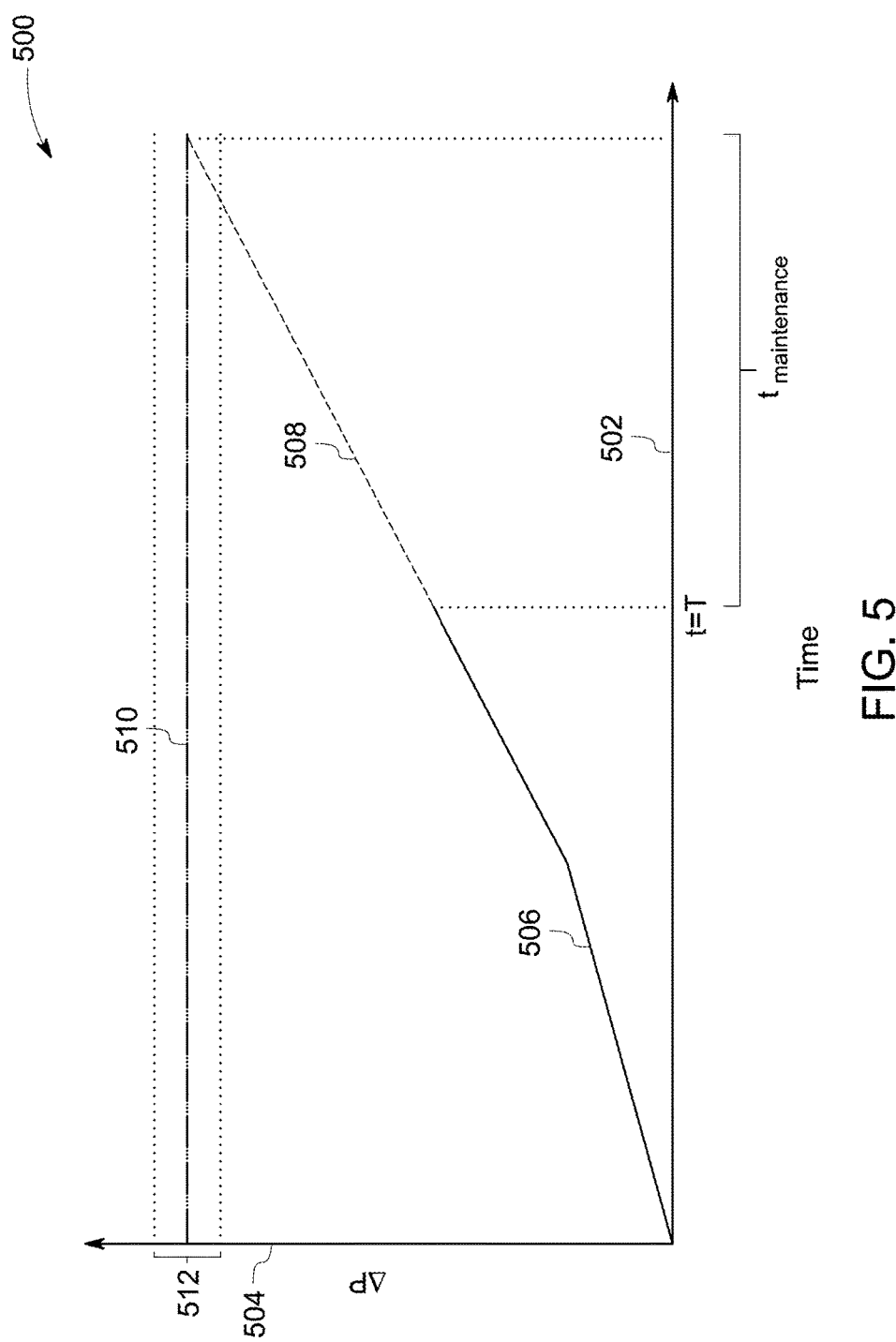
FIG. 5 is a graphical representation of an average pressure differential, in accordance with one embodiment of the present specification.

At step 404, the method includes determining a rate of change of the average pressure differential based on the average pressure differential values. In some embodiments, the MCS 112 may determine the rate of change of the average pressure differential. In order to determine the rate of change of the average pressure differential, the MCS 112 may store the received values of the average pressure differential over a period of time. FIG. 5 is a graphical representation 500 of the average pressure differential, in accordance with one embodiment of the present specification. In the graphical representation 500, the X-axis 502 represents time (hour or days) and the Y-axis 504 represent the average pressure differential values. A graph 506 represents variations in the average pressure differential over a period of time. In some embodiments, the MCS 112 may determine the rate of change of the average pressure differential as a slope of the graph 506.

Further, at step 406, the method 400 includes extrapolating the rate of change of the average pressure differential. The MCS 112 may extrapolate the rate of change of the average pressure differential to obtain to obtain an extrapolated average pressure differential (see FIG. 5). A graph 508 (shown using a dashed line), in FIG. 5, represents extrapolated average pressure differential. The MCS 112 may extrapolate the rate of change of the average pressure differential using techniques including, but not limited to, linear extrapolation, polynomial extrapolation, conic section extrapolation, French curve extrapolation, or combinations thereof.

Further, at step 408, the method 400 includes predicting a filter maintenance due time based on the extrapolated average pressure differential, the rate of change of the average pressure differential, and a target maintenance pressure differential. The filter maintenance due time is a time required for the extrapolated average pressure differential to attain a value within a predefined range from the target maintenance pressure differential. In a non-limiting example, the filter maintenance due time may indicate a number of days before which the filter 2a or 2b (depending on which one is active) is to be serviced or replaced.

As depicted in FIG. 5, a reference numeral 510 indicates the target maintenance pressure differential and the reference numeral 512 represents predefined range about the target maintenance pressure differential 510. At a given time t=T, the MCS 112 may calculate the filter maintenance due time as a time required for the extrapolated average pressure differential to attain a value within the predefined range 512 from the target maintenance pressure differential 510.

In some embodiments, the predefined range 512 may be a variable range, and may be defined by the operator of the underwater hydrocarbon well facility 100. In one non-limiting example, the predefined range 512 includes values of the average pressure differential within ±5% from the target maintenance pressure differential 510. In another non-limiting example, the predefined range 512 includes values of the average pressure differential within ±10% from the target maintenance pressure differential 510. In yet another non-limiting example, the predefined range 512 includes values of the average pressure differential within ±20% from the target maintenance pressure differential 510. In yet another non-limiting example, the predefined range 512 may be 0 (zero) which indicates that the filter maintenance due time is time required for the extrapolated average pressure differential 508 to attain a value equal to the target maintenance pressure differential 510.

In some embodiments, the MCS 112 computes the filter maintenance due time, by using equation (5):

$$t_{mainenance} = \frac{\Delta P_{maintenance} - \Delta P_{average}}{\Delta P_{rate\ of\ change}} \quad \text{Equation (5)}$$

where, $t_{maintenance}$ represents the filter maintenance due time, $\Delta P_{maintenance}$ represents the target maintenance pressure differential, $\Delta P_{average}$ represents the average pressure differential, and $\Delta P_{rate\ of\ change}$ represents the rate of change of the average pressure differential. In a non-limiting example, in the underwater hydrocarbon well facility 100, assume that a pressure of the hydraulic fluid from the hydraulic fluid source 1a is 5000 psi and a maximum allowable average pressure differential (i.e., the target maintenance pressure differential) is 200 psi. If the average pressure differential yesterday was 2 psi and the average pressure differential today is 3 psi, then the rate of change is 1 psi/day. Therefore, the filter maintenance due time is (200−3)/1=197 days. Accordingly, the filter can be used for 197 days before conducting maintenance.

Moreover, at step 410, the method 400 includes generating an indication of the predicted filter maintenance due time for the operator of the underwater hydrocarbon well facility 100. By way of example, generating the indication includes displaying a message on a display (not shown) associated with the MCS 112, producing an audio alarm, glowing a set of lighting emitting sources (not shown), sending a text message to the operator, sending a multimedia message to the operator, or combinations thereof.

Additionally, in certain embodiments, the MCS 112 may also monitor the rate of change of the average pressure differential. At step 412, the method 400, includes generating an alarm indicative of an increased level of clog in the filter if the rate of change of the average pressure differential exceeds a predefined threshold value. The MCS 112 compares the rate of change of the average pressure differential determined at step 404, with the predefined threshold value to determine whether the rate of change of the average pressure differential exceeds a predefined threshold value. The predefined threshold value may be indicative of the filter being excessively clogged and a requirement for immediate service and/or replacement of the clogged filter. In certain embodiments, if the rate of change of the average pressure differential exceeds the predefined threshold value, such an increased rate of change of the average pressure differential indicates an issue with one or more of the umbilicals 108, 110 or the UTAs 116.

This written description uses examples to disclose the specification, including the best mode, and also to enable any person skilled in the art to practice the specification, including making and using any devices or systems and performing any incorporated methods. The patentable scope of the specification is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:

1. A control system for monitoring a filter in a subsea control module of an underwater hydrocarbon well, wherein an input of the filter is connected to a hydraulic fluid source to receive a hydraulic fluid, and wherein the filter is configured to filter the hydraulic fluid, the control system comprising:
    an upstream pressure transducer disposed upstream of the filter and configured to sense an upstream pressure of the hydraulic fluid;
    a downstream pressure transducer disposed downstream of the filter and configured to sense a downstream pressure of the hydraulic fluid;
    a subsea electronics module coupled to the upstream pressure transducer and the downstream pressure transducer, and wherein the subsea electronics module is configured to determine average pressure differential values at different instances based on the upstream pressure and the downstream pressure; and
    a master control station coupled to the subsea electronics module and configured to:

receive the average pressure differential values from the subsea electronics module;

determine a rate of change of the average pressure differential based on the average pressure differential values;

extrapolate the rate of change of the average pressure differential to obtain an extrapolated average pressure differential;

predict a filter maintenance due time based on the extrapolated average pressure differential, the rate of change of the average pressure differential, and a target maintenance pressure differential; and generate an indication of the predicted filter maintenance due time for an operator of the underwater hydrocarbon well.

2. The control system of claim 1, wherein the filter maintenance due time is a time required for the extrapolated average pressure differential to attain a value within a predefined range from a target maintenance pressure differential, and wherein the predefined range comprises average pressure differential values in a range of ±20% from the target maintenance pressure differential.

3. The control system of claim 1, wherein the master control station is configured to predict the filter maintenance due time using equation:

$$t_{mainenance} = \frac{\Delta P_{maintenance} - \Delta P_{average}}{\Delta P_{rate\ of\ change}}$$

wherein $t_{maintenance}$ represents the filter maintenance due time, $\Delta P_{maintenance}$ represents the target maintenance pressure differential, $\Delta P_{average}$ represents the extrapolated average pressure differential, and $\Delta P_{rate\ of\ change}$ represents the rate of change of the average pressure differential.

4. The control system of claim 1, wherein the master control station is further configured to generate an alarm indicative of an increased level of clog in the filter if the rate of change of the average pressure differential exceeds a predefined threshold value.

5. The control system of claim 1, wherein the upstream pressure transducer is disposed between the hydraulic fluid source and the filter.

6. The control system of claim 1, wherein the downstream pressure transducer is coupled directly to an output of the filter.

7. The control system of claim 1, wherein the subsea control module further comprises a selector valve coupled to an output of the filter and configured to selectively enable a flow of the hydraulic fluid via the filter.

8. The control system of claim 7, wherein the downstream pressure transducer is disposed between the filter and the selector valve.

9. The control system of claim 7, wherein the downstream pressure transducer is disposed downstream of the selector valve.

10. The control system of claim 7, wherein the master control station is disposed outside the underwater hydrocarbon well.

11. A control system for monitoring a first filter and a second filter in a subsea control module of an underwater hydrocarbon well, wherein an input of the first filter is connected to a first hydraulic fluid source to receive a first hydraulic fluid and an input of the second filter is connected to a second hydraulic fluid source to receive a second hydraulic fluid, the control system comprising:

a first upstream pressure transducer disposed upstream of the first filter and configured to sense a first upstream pressure of the first hydraulic fluid, wherein the first filter is disposed in a first hydraulic flow path of the subsea control module;

a second upstream pressure transducer disposed upstream of the second filter and configured to sense a second upstream pressure of the second hydraulic fluid, wherein the second filter is disposed in a second hydraulic flow path of the subsea control module;

a first downstream pressure transducer coupled directly to an output of the first filter and configured to sense a first downstream pressure of the first hydraulic fluid;

a second downstream pressure transducer coupled directly to an output of the second filter and configured to sense a second downstream pressure of the second hydraulic fluid;

a subsea electronics module coupled to the first upstream pressure transducer, the first downstream pressure transducer, the second upstream pressure transducer, and the second downstream pressure transducer, wherein the subsea electronics module is configured to determine average pressure differential values at different instances based the first upstream pressure and the first downstream pressure or the second upstream pressure and the second downstream pressure; and a master control station coupled to the subsea electronics module and configured to:

receive the average pressure differential values from the subsea electronics module;

determine a rate of change of the average pressure differential based on the average pressure differential values;

extrapolate the rate of change of the average pressure differential to obtain an extrapolated average pressure differential;

predict a filter maintenance due time based on the extrapolated average pressure differential, the rate of change of the average pressure differential, and a target maintenance pressure differential; and generate an indication of the predicted filter maintenance due time for an operator of the underwater hydrocarbon well.

12. The control system of claim 11, wherein the subsea control module further comprises:

a first selector valve coupled to the output of the first filter and configured to selectively enable a flow of the first hydraulic fluid via the first filter; and a second selector valve coupled to the output of the second filter and configured to selectively enable a flow of the second hydraulic fluid via the second filter.

13. The control system of claim 11, wherein the first hydraulic fluid is same as the second hydraulic fluid.

14. The control system of claim 11, wherein the subsea electronics module comprises a subsea electronics module coupled to the first upstream pressure transducer, the first downstream pressure transducer, the second upstream pressure transducer, and the second downstream pressure transducer.

15. A method for monitoring a filter in a subsea control module of an underwater hydrocarbon well, wherein an input of the filter is connected to a hydraulic fluid source to receive a hydraulic fluid, the method comprising:

receiving average pressure differential values from a subsea electronics module, wherein the subsea electronics module is coupled to an upstream pressure transducer disposed upstream of the filter and a downstream pressure transducer disposed downstream of the filter;

determining a rate of change of the average pressure differential based on the average pressure differential values;

extrapolating the rate of change of the average pressure differential to obtain an extrapolated average pressure differential;

predicting a filter maintenance due time based on the extrapolated average pressure differential, the rate of change of the average pressure differential, and a target maintenance pressure differential; and generating an indication of the predicted filter maintenance due time for an operator of the underwater hydrocarbon well.

16. The method of claim 15, wherein the filter maintenance due time is a time required for the extrapolated average pressure differential to attain a value within a predefined range from a target maintenance pressure differential, and wherein the predefined range comprises average pressure differential values in a range of ±20% from the target maintenance pressure differential.

17. The method of claim 15, wherein predicting the filter maintenance due time comprises determining the filter maintenance due time using equation:

$$t_{mainenance} = \frac{\Delta P_{maintenance} - \Delta P_{average}}{\Delta P_{rate\ of\ change}}$$

wherein $t_{maintenance}$ represents the filter maintenance due time, $\Delta P_{maintenance}$ represents the target maintenance pressure differential, $\Delta P_{average}$ represents the extrapolated average pressure differential, and $\Delta P_{rate\ of\ change}$ represents the rate of change of the average pressure differential.

18. The method of claim 15, further comprising generating an alarm indicative of an increased level of clog in the filter if the rate of change of the average pressure differential exceeds a predefined threshold value.

19. The method of claim 15, wherein generating an indication of the predicted filter maintenance due time comprises displaying a message on a display, producing an audio alarm, glowing a set of lighting emitting sources, sending a text message to the operator, sending a multimedia message to the operator, or combinations thereof.

20. The method of claim 15, further comprising determining average pressure differential values by the subsea electronics module based on an upstream pressure sensed by the upstream pressure transducer and a downstream pressure sensed by the downstream pressure transducer.

* * * * *